United States Patent
Berry et al.

(10) Patent No.: US 9,552,529 B2
(45) Date of Patent: *Jan. 24, 2017

(54) ANALYSIS OF ELECTROPHORETIC BANDS IN A SUBSTRATE

(71) Applicant: Pierce Biotechnology, Inc., Rockford, IL (US)

(72) Inventors: Rachael Mae Berry, Winnebago, IL (US); Nikki L. Jarrett, Roscoe, IL (US); Eric Leigh Hommema, Roscoe, IL (US); Kelli D. Feather-Henigan, Winnebago, IL (US); Suk J. Hong, Roscoe, IL (US); Brian Lynn Webb, Roscoe, IL (US)

(73) Assignee: PIERCE BIOTECHNOLOGY, INC., Rockford, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/955,475

(22) Filed: Dec. 1, 2015

(65) Prior Publication Data

US 2016/0117565 A1  Apr. 28, 2016

Related U.S. Application Data

(63) Continuation of application No. 13/786,976, filed on Mar. 6, 2013, now Pat. No. 9,230,185.

(60) Provisional application No. 61/617,819, filed on Mar. 30, 2012.

(51) Int. Cl.
| | | |
|---|---|---|
| G06K 9/36 | (2006.01) | |
| G06K 9/40 | (2006.01) | |
| G01N 21/84 | (2006.01) | |
| G01N 27/447 | (2006.01) | |
| G06T 11/60 | (2006.01) | |

(52) U.S. Cl.
CPC ............ *G06K 9/40* (2013.01); *G01N 21/8483* (2013.01); *G01N 27/447* (2013.01); *G06K 9/36* (2013.01); *G06T 11/60* (2013.01); *G01N 2201/12* (2013.01)

(58) Field of Classification Search
None
See application file for complete search history.

(56) References Cited

U.S. PATENT DOCUMENTS

| | | | | |
|---|---|---|---|---|
| 5,242,567 A * | 9/1993 | Fujimiya | ........ | G01N 27/44721 204/612 |
| 5,800,992 A * | 9/1998 | Fodor | ........... | B01J 19/0046 435/6.12 |
| 6,064,754 A * | 5/2000 | Parekh | ........... | G01N 27/44704 382/129 |
| 6,211,913 B1 | 4/2001 | Hansen et al. | | |
| 6,301,377 B1 * | 10/2001 | Taylor, Jr. | ........... | G06K 9/6206 382/129 |

(Continued)

OTHER PUBLICATIONS

AlphaImager HP EP and EC User Guide, 2010.

*Primary Examiner* — Sean Motsinger
(74) *Attorney, Agent, or Firm* — Michael J. Smith

(57) ABSTRACT

A method and system to enhance analysis of electrophoretic bands by overlaying only the pixels of interest. The overlaid pixels are superimposed as a layer above, i.e., in the foreground of, the overlaid image, i.e., in the background. A user employs the superimposed pixels for molecular weight determination and is still able to generate densitometry analysis of the remaining pixels in the overlaid image.

20 Claims, 19 Drawing Sheets

(56) References Cited

U.S. PATENT DOCUMENTS

| | | | |
|---|---|---|---|
| 6,535,624 B1* | 3/2003 | Taylor, Jr. | G06T 3/4053 382/128 |
| 8,977,558 B2* | 3/2015 | Nielsen | G06Q 10/103 701/491 |
| 2002/0118893 A1* | 8/2002 | Nguyen | G01N 21/9515 382/294 |
| 2003/0077832 A1* | 4/2003 | Fritsche | G01N 33/57415 436/64 |
| 2003/0198385 A1* | 10/2003 | Tanner | G06K 9/00 382/195 |
| 2004/0219545 A1* | 11/2004 | Rando | B82Y 30/00 435/6.12 |
| 2005/0239122 A1* | 10/2005 | Afar | C12Q 1/6886 435/6.14 |
| 2006/0068036 A1* | 3/2006 | Wu | A61K 36/8945 424/725 |
| 2006/0257053 A1* | 11/2006 | Boudreau | G06T 7/0012 382/305 |
| 2007/0225228 A1* | 9/2007 | Watkins | C12N 5/0622 514/8.3 |
| 2008/0003224 A1* | 1/2008 | Fong | C07K 16/289 424/139.1 |
| 2008/0144932 A1* | 6/2008 | Chien | G06K 9/4671 382/169 |
| 2010/0069252 A1* | 3/2010 | Chibber | C40B 60/10 506/7 |
| 2010/0171760 A1 | 7/2010 | Itkin | |
| 2013/0109027 A1* | 5/2013 | Kiss | C12N 15/101 435/6.12 |
| 2013/0156279 A1* | 6/2013 | Schoenmeyer | G06T 7/0028 382/128 |
| 2013/0288388 A1* | 10/2013 | Freeby | G01N 33/6827 436/501 |

* cited by examiner

Imager Information

| Creation Date | 12/1/2011 1:53:45 PM |
| --- | --- |
| User Name | Jarrett, Nikki L. |
| Image Area (mm) | X: 57.743 Y: 57.743 |
| Image Pixels | X: 682 Y: 682 |
| Pixel Size (um) | X: 11.811 Y: 11.811 |

FIGURE 13 continued
Molecular Weight Analysis Details

| Standard | PageRuler Plus Prestained Protein Ladder |
|---|---|
| Standard Lanes | 1 |
| Regression Method | Linear (semi-log) |

Imager Information

General Information

| Creation | 12/1/2011 1:53:45 PM |
|---|---|
| Application | 1.0 |

Sensitivity

| Binning | 3, 3 |
|---|---|

Capture Settings

| Acquisition | 2011/12/01 |
|---|---|
| Acquisition | 1:53 PM |
| Exposure | Single |
| Exposure | 10s |
| File Name | ChemiS 10s 20111201 1353.tif |
| Folder Name | ChemiS 10s 20111201 1353 |
| Image Name | gst |
| Instrument | Fast Imager |
| Modified | No |
| Project | |
| Serial | KR01211106 |
| Temperature | -24.9 C |
| User | |
| Experiment | |

FIGURE 13 continued

LANE AND BAND ANALYSIS

Lane 1
"All Data" analysis results table

| Band Id | Volume (Intensity) | Area (Pixels) | Density (Intensity/area) | Median (Intensity) | Local Bkg Corr. Volume (Intensity) | Local Bkg Corr. Density (Intensity/Area) | Rf | MW (kDa) | Calc. MW (kDa) | % Purity | % Purity (Lane) |
|---|---|---|---|---|---|---|---|---|---|---|---|
| 1 | 216572 | 226 | 958 | 865 | 33271.00 | 147.22 | 0.101 | 250 | 250.00 | 11.03 | 3.40 |
| 2 | 108192 | 100 | 1081 | 865 | 29752.00 | 297.52 | 0.130 | 130 | 130.00 | 9.86 | 1.70 |
| 3 | 152502 | 150 | 1016 | 869 | 30877.00 | 205.85 | 0.188 | 100 | 100.00 | 10.24 | 2.40 |
| 4 | 151885 | 150 | 1012 | 866 | 31910.00 | 212.73 | 0.229 | 70 | 70.00 | 10.58 | 2.39 |
| 5 | 195442 | 201 | 972 | 866 | 33522.00 | 166.78 | 0.317 | 55 | 55.00 | 11.11 | 3.07 |
| 6 | 370303 | 402 | 921 | 868 | 36442.00 | 90.65 | 0.396 | 35 | 35.00 | 12.08 | 5.82 |
| 7 | 368068 | 402 | 915 | 864 | 35559.00 | 88.46 | 0.471 | 25 | 25.00 | 11.79 | 5.79 |
| 8 | 389919 | 427 | 913 | 866 | 35843.00 | 83.94 | 0.541 | 15 | 15.00 | 11.88 | 6.13 |
| 9 | 281850 | 301 | 936 | 864 | 34495.00 | 114.60 | 0.628 | 10 | 10.00 | 11.43 | 4.43 |
| Band Detection | | | | | Sensitivity: 99% | | | | | | |

Lane 2
"All Data" analysis results table

| Band Id | Volume (Intensity) | Area (Pixels) | Density (Intensity/area) | Median (Intensity) | Local Bkg Corr. Volume | Local Bkg Corr. Density (Intensity/Area) | Rf | Calc. MW (kDa) | % Purity | % Purity (Lane) |
|---|---|---|---|---|---|---|---|---|---|---|
| 1 | 721364 | 125 | 5770 | 4961 | 563171.00 | 4505.37 | 0.169 | 122.28 | 87.47 | 9.98 |
| 2 | 211727 | 150 | 1411 | 1218 | 80677.00 | 537.85 | 0.297 | 60.37 | 12.53 | 2.93 |
| Band Detection | | | | | | Sensitivity: 99% | | | | |
| Regression Equation | | | | | | Y= -2.40 * X + 2.49  R-squared value: 0.867649 | | | | |

FIGURE 13 continued

Lane 3
"All Data" analysis results table

| Band Id | Volume (Intensity) | Area (Pixels) | Density (Intensity/area) | Median (Intensity) | Local Bkg. Corr. Volume | Local Bkg. Corr. Density (Intensity/Area) | Rf | Calc. MW (kDa) | % Purity | % Purity (Lane) |
|---|---|---|---|---|---|---|---|---|---|---|
| 1 | 680943 | 125 | 5447 | 4805 | 515954.00 | 4127.63 | 0.165 | 124.61 | 13.95 | 5.82 |
| 2 | 3638709 | 150 | 24258 | 22371 | 3183496.00 | 21223.31 | 0.242 | 81.59 | 86.05 | 31.09 |
| Band Detection | | | | | | Sensitivity: 99% | | | | |
| Regression Equation | | | | | | Y= -2.40 * X + 2.49  R-squared value: 0.867649 | | | | |

Lane 4
"All Data" analysis results table

| Band Id | Volume (Intensity) | Area (Pixels) | Density (Intensity/area) | Median (Intensity) | Local Bkg. Corr. Volume | Local Bkg. Corr. Density (Intensity/Area) | Rf | Calc. MW (kDa) | % Purity | % Purity (Lane) |
|---|---|---|---|---|---|---|---|---|---|---|
| 1 | 1649406 | 201 | 8206 | 7281 | 1181765.00 | 5879.43 | 0.160 | 128.18 | 22.48 | 10.62 |
| 2 | 4907885 | 276 | 17782 | 16493 | 4074933.00 | 14764.25 | 0.196 | 105.19 | 77.52 | 31.59 |
| Band Detection | | | | | | Sensitivity: 99% | | | | |
| Regression Equation | | | | | | Y= -2.40 * X + 2.49  R-squared value: 0.867649 | | | | |

FIGURE 13 continued

Lane 5
"All Data" analysis results table

| Band Id | Volume (Intensity) | Area (Pixels) | Density (Intensity/area) | Median (Intensity) | Local Bkg. Corr. Volume (Intensity) | Local Bkg. Corr. Density (Intensity/Area) | Rf | Calc. MW (kDa) | % Purity | % Purity (Lane) |
|---|---|---|---|---|---|---|---|---|---|---|
| 1 | 619455 | 100 | 6194 | 5500 | 474775.00 | 4747.75 | 0.157 | 130.61 | 7.20 | 3.74 |
| 2 | 5797230 | 176 | 32938 | 35904 | 4743166.00 | 26949.81 | 0.309 | 56.52 | 71.90 | 34.97 |
| 3 | 514291 | 125 | 4114 | 4191 | 322302.00 | 2578.42 | 0.360 | 42.62 | 4.89 | 3.10 |
| 4 | 1387196 | 201 | 6901 | 6341 | 1056393.00 | 5255.69 | 0.437 | 27.90 | 16.01 | 8.37 |
| Band Detection | | | | | Sensitivity: 99% | | | | | |
| Regression Equation | | | | | Y= -2.40 * X + 2.49  R-squared value: 0.867649 | | | | | |

Lane 6
"All Data" analysis results table

| Band Id | Volume (Intensity) | Area (Pixels) | Density (Intensity/area) | Median (Intensity) | Local Bkg. Corr. Volume | Local Bkg. Corr. Density (Intensity/Area) | Rf | Calc. MW (kDa) | % Purity | % Purity (Lane) |
|---|---|---|---|---|---|---|---|---|---|---|
| 1 | 690300 | 125 | 5522 | 4563 | 526470.00 | 4211.76 | 0.159 | 129.39 | 8.81 | 3.99 |
| 2 | 6478630 | 150 | 43190 | 44902 | 5446705.00 | 36311.37 | 0.280 | 66.33 | 91.19 | 37.48 |
| Band Detection | | | | | Sensitivity: 99% | | | | | |
| Regression Equation | | | | | Y= -2.40 * X + 2.49  R-squared value: 0.867649 | | | | | |

FIGURE 13 continued

Lane 7
"All Data" analysis results table

| Band Id | Volume (Intensity) | Area (Pixels) | Density (Intensity/area) | Median (Intensity) | Local Bkg. Corr. Volume | Local Bkg. Corr. Density (Intensity/Area) | Rf | Calc. MW (kDa) | % Purity | % Purity (Lane) |
|---|---|---|---|---|---|---|---|---|---|---|
| 1 | 690388 | 100 | 6903 | 6300 | 541478.00 | 5414.78 | 0.164 | 125.79 | 10.88 | 4.85 |
| 2 | 5191262 | 150 | 34608 | 35626 | 4435700.00 | 29571.33 | 0.249 | 78.57 | 89.12 | 36.47 |
| Band Detection | | | | | Sensitivity: 99% | | | | | |
| Regression Equation | | | | | Y= -2.40 * X + 2.49<br>R-squared value: 0.867649 | | | | | |

Lane 8
"All Data" analysis results table

| Band Id | Volume (Intensity) | Area (Pixels) | Density (Intensity/area) | Median (Intensity) | Local Bkg. Corr. Volume | Local Bkg. Corr. Density (Intensity/Area) | Rf | Calc. MW (kDa) | % Purity | % Purity (Lane) |
|---|---|---|---|---|---|---|---|---|---|---|
| 1 | 1370340 | 226 | 6063 | 4978 | 987858.00 | 4371.05 | 0.169 | 122.28 | 16.49 | 7.74 |
| 2 | 6033354 | 201 | 30016 | 31422 | 5002554.00 | 24888.33 | 0.266 | 71.51 | 83.51 | 34.08 |
| Band Detection | | | | | Sensitivity: 99% | | | | | |
| Regression Equation | | | | | Y= -2.40 * X + 2.49<br>R-squared value: 0.867649 | | | | | |

Lane 9
"All Data" analysis results table

| Band Id | Volume (Intensity) | Area (Pixels) | Density (Intensity/area) | Median (Intensity) | Local Bkg. Corr. Volume | Local Bkg. Corr. Density (Intensity/Area) | Rf | Calc. MW (kDa) | % Purity | % Purity (Lane) |
|---|---|---|---|---|---|---|---|---|---|---|
| 1 | 1309299 | 201 | 6513 | 4969 | 938856.00 | 4670.93 | 0.177 | 116.66 | 27.73 | 10.55 |
| 2 | 2614041 | 150 | 17426 | 16207 | 2191841.00 | 14612.27 | 0.212 | 96.65 | 64.74 | 21.07 |
| 3 | 494305 | 226 | 2187 | 2128 | 255167.00 | 1129.06 | 0.408 | 32.75 | 7.54 | 3.98 |
| Band Detection | | | | | Sensitivity: 99% | | | | | |
| Regression Equation | | | | | Y= -2.40 * X + 2.49<br>R-squared value: 0.867649 | | | | | |

FIGURE 13 continued

Lane 10

"All Data" analysis results table

| Band Id | Volume (Intensity) | Area (Pixels) | Density (Intensity/area) | Median (Intensity) | Local Bkg. Corr. Volume | Local Bkg. Corr. Density (Intensity/Area) | Rf | Calc MW (kDa) | % Purity | % Purity (Lane) |
|---|---|---|---|---|---|---|---|---|---|---|
| 1 | 864368 | 125 | 6914 | 6110 | 655925.00 | 5247.40 | 0.179 | 115.57 | 9.86 | 4.76 |
| 2 | 7444803 | 201 | 37038 | 37287 | 5998680.00 | 29844.18 | 0.304 | 58.14 | 90.14 | 41.00 |
| Band Detection || | | | Sensitivity: 99% ||||||
| Regression Equation || | | | Y= -2.40 * X + 2.49<br>R-squared value: 0.867649 ||||||

Lane 11
"All Data" analysis results table

| Band Id | Volume (Intensity) | Area (Pixels) | Density (Intensity/area) | Median (Intensity) | Local Bkg. Corr. Volume | Local Bkg. Corr. Density (Intensity/Area) | Rf | Calc MW (kDa) | %Purity | %Purity (Lane) |
|---|---|---|---|---|---|---|---|---|---|---|
| 1 | 891604 | 125 | 7132 | 6796 | 694479.00 | 5555.83 | 0.186 | 111.30 | 100.00 | 11.63 |
| Band Detection || | | | Sensitivity: 99% ||||||
| Regression Equation || | | | Y= -2.40 * X + 2.49<br>R-squared value: 0.867649 ||||||

ANALYSIS OF ELECTROPHORETIC BANDS IN A SUBSTRATE

This application claims priority to U.S. application Ser. No. 13/786,976 filed Mar. 6, 2013 now U.S. Pat. No. 9,230,185 and U.S. Application Ser. No. 61/617,819 filed Mar. 30, 2012, each of which is expressly incorporated by reference herein in its entirety.

A method and system to visualize and analyze target objects from two different images of the same substrate acquired by a charge coupled device (CCD) imager. The method and system improved band detection by superimposing molecular weight markers, detected with a first visualizing means, over analyte bands, detected with a second visualizing means.

BRIEF DESCRIPTION OF THE DRAWINGS

The patent or application file contains at least one drawing executed in color. A Petition under 37 C.F.R. §1.84 requesting acceptance of the color drawing is being filed separately. Copies of this patent or patent application publication with color drawing(s) will be provided by the Office upon request and payment of the necessary fee.

Figure 1:
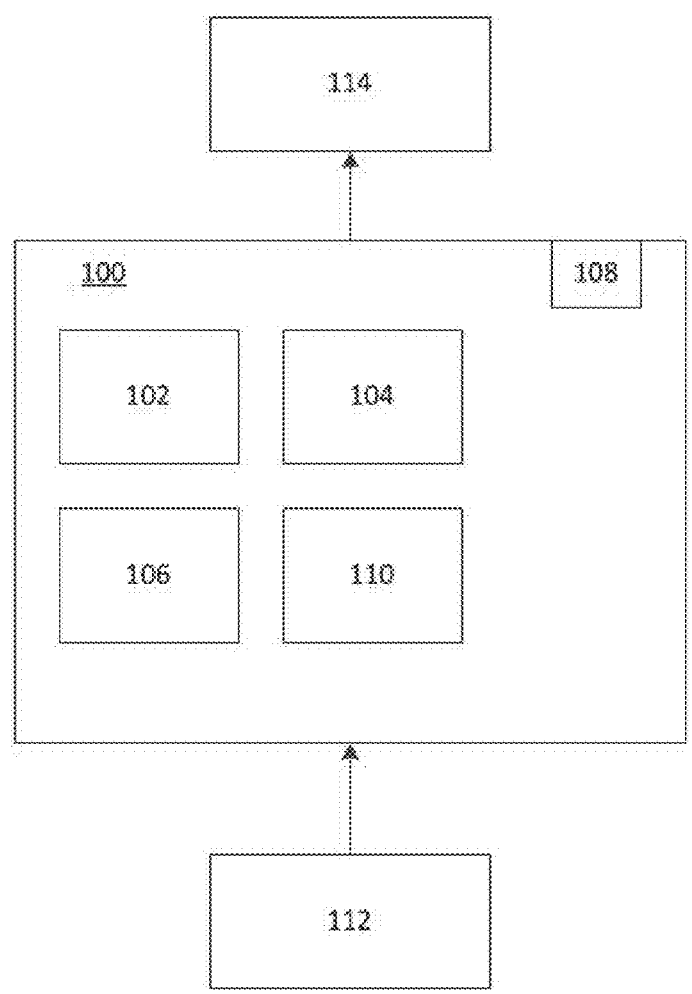
FIG. 1 diagrams a general purpose computer system suitable for operating the inventive method and system.

Life science researchers routinely image stained gel electrophoresis samples and Western blots for data analysis. To perform electrophoretic separation of complex mixtures, several samples containing these mixtures are applied to the electrophoresis gel in separate locations. When an electrical current is applied, the individual samples migrate vertically down the gel within their prescribed vertical lane or track, and generate an invisible lane on the gel. The complex mixture is then separated by size, i.e., molecular weight, in the gel matrix. The larger, higher molecular weight molecules remain relatively nearer the top of the gel or membrane. The smaller, lower molecular weight molecules migrate toward the bottom of the gel or membrane. Each individual segregation is then identified as a band. The gel can then be stained for total sample visualization, or transferred to a membrane for visualization of a specific target of interest by Western blotting. The researcher then images the gel or blot, collectively termed a substrate, to analyze the target(s) of interest for amount, relative or absolute, purity, and molecular weight. Such analysis requires detection and identification of the lanes and bands in the image.

Two images of the same substrate are typically required using different visualization means, such as white light illumination, fluorescence, or chemiluminescence. With Western blots, objects in one image, such as protein molecular weight markers located on one area of the substrate, are stained with a visible dye; and objects from the other image, such as biological samples located on other areas of the substrate, are detected by antibody-based chemiluminescent or fluorescent techniques. The stained molecular weight markers located in one or more lanes on the blot are visualized by white light illumination and the biological samples located in other lanes on the blot are visualized using chemiluminescence. Thus, two corresponding images of the same substrate are captured with the exact same view of the substrate, but with different visualization methods.

Molecular weight size markers typically are a set of molecules of known size, i.e., molecular weights. If such a marker set was applied to one lane in a gel and separated by electrophoresis, parallel to the unknown samples, the vertical positions of the bands observed in the molecular weight marker set can be compared to the vertical positions of the bands in the unknown sample in order to determine the molecular weight of the molecules in the unknown sample. The relative amount of each band is calculated by comparing its signal intensity to that of other bands. The absolute amount of a band is calculated by comparing signal intensity to bands of known quantity.

Existing image analysis technology allows overlaying two or more complete images to generate an overall composite image, facilitating molecular weight determination by comparing vertical positions between the two images. However, analysis of relative areas must be performed on a single image at a time. Commercial image analysis software permits creation of a composite image by adding pixel intensities at each corresponding location on the images, but this prevents accurate analysis because the pixels in the overlaid image will have the pixel values from the superimposed image included in the analysis.

Publicly available ImageJ software can create a composite image or image stack from images acquired in different color channels or multiple grayscale images of the same sample, but this composite image cannot be analyzed. ProteinSimple's AlphaView software can overlay images to create a RGB image, but again the resulting composite image cannot be analyzed. Syngene's GeneSnap software can acquire images of the same substrate by different detection methods and then create a composite image from two or three original images. The composite image can then be analyzed by Syngene's GeneSnap or GeneTools Software functions. However, since the created composite image is achieved by pixel addition, any subsequent band analysis is compromised. The software user manual states that such images "do not satisfy the conditions required for Good Laboratory Practice" and that this is noted in the image's capture properties. Hence these composite images should not be used for densitometry analysis and are only appropriate for molecular weight determination of the samples.

The inventive system allows a user to perform the necessary molecular weight analyses from data shared between the two images, while retaining the ability to evaluate the accurate, undistorted densitometry data from one of the images at a time.

In one embodiment, the method and system overlays only the pixels of interest, where the superimposed pixels exist as a layer above, i.e., in the foreground, the overlaid image, i.e., the background. The user is thus able to employ the superimposed pixels for other types of analysis, e.g., molecular weight determination, and is still able to generate densitometry analysis of the remaining pixels in the overlaid image.

In one embodiment, the method and system overlays selected pixels from one image onto the corresponding location of the other image. This pixel overlay allows objects from the two different images to be visualized at the same time in a resulting composite image. It allows objects from the two images to be analyzed independently on the composite image, and allows the user to interact with, e.g., draw and adjust a lane frame or other region of interest) both images simultaneously.

The two images of the same substrate are typically acquired using different visualization means, such as white light illumination, fluorescence, or chemiluminescence.

In one embodiment of the system, the computer displays both images to the user simultaneously during the process used to create the area of pixel overly. In this embodiment, the software shows both images to the user. As the user draws the lane frame on the first image, that same lane frame is shown in the corresponding location on the second image. The first and second images are thus "linked", so that the lane frame is exactly as the user desires before the user indicates to the software which lane to overlay. This embodiment minimizes or avoids the need for the user to adjust the lane frame after the fact if it were not as the user desired.

The method and system is used for life science applications. Protein molecular weight markers electrophoretically separated are located in one area of a substrate, and are typically stained with a visible dye. Test or analyte samples electrophoretically separated are located in other areas of a substrate and are typically detected by antibody-based chemiluminescent or fluorescent techniques. In this embodiment, the separated stained molecular weight markers are typically visualized by white light illumination; the separated test or analyte samples are typically visualized by fluorescence or chemiluminescence. Thus, two corresponding images of the same substrate are captured with the exact same view of the substrate but with different visualization methods.

In use, the user-defined pixels from the first image are then overlaid by the software onto the corresponding pixels from the second image, generating a new composite image. In the composite image, the superimposed pixels exist as a layer above, i.e., in the foreground of, the overlaid image, i.e., in the background. This composite image enables visualization and analysis of the superimposed objects independently of the objects on the overlaid image. For example, the superimposed pixels containing the molecular weight marker lane on a blot can be used to determine the relative position of the markers on the blot and this information can be used to estimate the molecular weights of protein bands from biological samples visualized by chemiluminescence in other lanes in the overlaid image. The protein bands in other lanes on the overlaid image can then be analyzed using densitometry to determine the relative abundance of these proteins. The user utilizes the superimposed pixels for one type of analysis, e.g., molecular weight determination, and is still able to generate densitometry analysis of the remaining pixels in the overlaid image. This process is enabled by a CCD imager programmed to automatically acquire a visible image prior to acquiring a chemiluminescence or fluorescent image. Thus both images are taken of the same substrate with identical substrate location and orientation. This automatic visible image acquisition feature can be performed without any user input and allows subsequent overlay and band analysis as described above. The combination of automatic visible image acquisition in the hardware and the overlay analysis in the software provides user convenience and utility.

In one embodiment, the inventive method uses an algorithm to enhance analysis and enable automatic identification of bands on a gel or blot by removing noise from the identified objects or bands. The method uses optimized threshold values, where a user-defined portion of one image is superimposed on another image in such a way that the pixel values from the two images are maintained, the composite image with the user-defined portion of the superimposed image is simultaneously displayed on top of the overlaid image, image analysis is performed on the composite image, i.e., molecular weight determination is performed on the superimposed image, which can be applied to the overlaid image lanes, and accurate, undistorted densitometry can be performed on the underlying image without the additive pixel values from the superimposed image.

In one embodiment, the method and system are used with results from a blotting procedure. In a blotting procedure, proteins and/or nucleic acids (deoxyribonucleic acids (DNA) and/or ribonucleic acids (RNA)) in a biological sample are first electrophoretically separated from each other, typically based upon their size, on a substrate or medium such as a sodium dodecyl sulfate-polyacrylamide gel. Next, a detectable probe that binds to a specific protein (s) or nucleic acid(s), or type of protein(s) or nucleic acid(s), is contacted with the substrate or medium. The probe may be, e.g., an antibody that specifically binds to a protein. The probe may be labeled with a compound that renders it detectable, e.g., a chemiluminescent compound detected by its chemiluminescence. Other ways to detect a probe are known to a person skilled in the art and include, but are not limited to, radioisotope labeling of the probe and detection by scintillation counting.

Protein(s), DNAs, and/or RNAs of interest are separated and then detected in blotting procedures (Western, Southern, and Northern blots, respectively). The results of the blotting procedure appear as a ladder where rungs of the ladder are the separated proteins or nucleic acids. If the labeled probe is bound, these rungs are visualized when the appropriate detection means are used (e.g., chemiluminescent probes are detectable upon chemiluminescent detection). The location(s) of the protein(s) or nucleic acid step(s) in the analyzed sample is compared to the location of the protein(s) or nucleic acid(s) steps in a control sample containing qualitatively and/or quantitatively known protein(s) and/or nucleic acid(s). Label detection permits identification of the presence, size, and/or concentration of the protein(s) or nucleic acid(s) based on the location and/or intensity of the signal. The pattern produced by this procedure is captured and recorded using an image capturing device such as autoradiography film, charge-coupled device (CCD) camera, scanner, phosphor imager, or other capture device known to a person skilled in the art. A durable copy of the image, termed a blot, records the results, permitting data comparison, memorialization, etc.

CCD cameras are a method of choice for image capture of scientific research results such as those from SDS-PAGE gel staining and blotting methods (Western, Northern and Southern). A common detection method utilized for identifying a target of interest in a blotting assay is chemiluminescence. However the most common control samples containing known protein(s), called molecular weight markers, are visibly labeled thus rendering them unable to be viewed by chemiluminescence. Historically, the signal generated from chemiluminescent blots has been captured using X-ray or autoradiography film. Results of the molecular weight markers are hand-drawn onto the exposed film with permanent ink and are only able to be used for qualitative approximation of size and/or amount of the protein(s) or nucleic acid(s) based on the location and/or intensity of the signal. Advances in digital imaging technology have made it possible to obtain results using instrumentation that captures a digital image, versus using conventional film. New image capture devices such as CCD camera systems improve image quality compared to film.

To enhance a researcher's ability to obtain a chemiluminescent signal from a blot and a visible signal from a stained molecular weight marker, the inventive methods and systems automatically acquire a visible image of every blot imaged in the chemiluminescence acquisition mode. The visible image is taken with white light illumination. The chemiluminescent image is acquired without illumination. Thus the images are taken of the same sample with identical sample locations. These images are then processed by the inventive overlay method to identify the presence, size, and/or concentration of the protein(s) and/or nucleic acid(s). Images from other instrumentation can be used only if the user manually acquires the two images of the same gel using different detection methods (i.e., white illumination and chemiluminescence or fluorescence) with identical sample location. In contrast, the inventive methods and systems automatically perform this function.

In one embodiment, the inventive method and system combines information from two images of the same blot or sample, shown in the following steps: open image, detect objects on image using object detection algorithm, retain the target objects and triage noise objects using threshold, determine lanes by tracking the vertically aligned objects from the top line of image, display lane and band perimeters. In another embodiment, the steps are: open images, perform image adjustments, create and adjust lane frame, identify image for superimposition, locate lane to be superimposed, identity molecular weight marker, and regression method to be used, detect objects on image using object detection algorithm, retain the target objects and triage noise objects using threshold, determine lanes by tracking the vertically aligned objects from the top line of image, software calculates analysis results that are displayed in an analysis table. Invention implementation in the software program includes placement and adjustment of the lane frame only while viewing the overlaid image, or while viewing both images (the lane frame can be viewed and adjusted simultaneously on both images as the information is linked).

The inventive methods and systems improved band detection by superimposing molecular weight markers, detected with a first visualizing means, over analyte bands, detected with a second visualizing means. Embodiments include a method, data processing system and/or computer program product. Thus, one embodiment is entirely hardware with logic embedded in circuitry, one embodiment is entirely software with logic operating on a general purpose computer to perform the method and operate the system, and/or one embodiment combines software and hardware aspects. One embodiment takes the form of a computer program product on a computer-readable storage medium having computer readable program code means embodied in the medium. Any suitable computer readable medium may be used including hard disks, CD-ROMs, optical storage devices, static or nonvolatile memory circuitry, or magnetic storage devices and the like. The executable program may be available for download from a website.

FIG. 1 shows an exemplary computer system 100 that can be used to implement the method and system. The computer system can be a laptop, desktop, server, handheld device (e.g., personal digital assistant (PDA), smartphone), programmable consumer electronics or programmable industrial electronics.

As illustrated the computer system includes a processor 102 that can be any various available microprocessors. For example, the processor can be implemented as dual microprocessors, multi-core and other multiprocessor architectures. The computer system includes memory 104 that can include volatile memory, nonvolatile memory or both. Nonvolatile memory can include read only memory (ROM) for storage of basic routines for transfer of information, such as during computer boot or start-up. Volatile memory can include random access memory (RAM). The computer system can include storage media 106 including, but not limited to, magnetic or optical disk drives, flash memory, and memory sticks. The computer system incorporates one or more interfaces, including ports 108 (e.g., serial, parallel, PCMCIA, USB, FireWire) or interface cards 110 (e.g., sound, video, network, etc.) or the like. In embodiments, an interface supports wired or wireless communications. Input is received from any number of input devices 112 (e.g., keyboard, mouse, joystick, microphone, trackball, stylus, touch screen, scanner, camera, satellite dish, another computer system and the like). The computer system outputs data through an output device 114, such as a display (e.g. CRT, LCD, plasma), speakers, printer, another computer or any other suitable output device.

The following description references flowchart illustrations of methods, apparatus (systems) and computer program products. It will be understood that each block of the flowchart illustrations, and combinations of blocks in the flowchart illustrations, can be implemented by computer program instructions. These computer program instructions may be loaded onto a computer or other programmable data processing apparatus or otherwise encoded into a logic device to produce a machine, such that the instructions which execute on the computer or other programmable data processing apparatus create means for implementing the functions specified in the flowchart block or blocks. These computer program instructions may also be stored in a computer readable memory that can direct a computer or other programmable data processing apparatus to function in a particular manner, such that the instructions stored in the computer readable memory produce an article of manufacture including instruction means that implement the function specified in the flowchart block or blocks. The computer program instruction may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Figure 2:
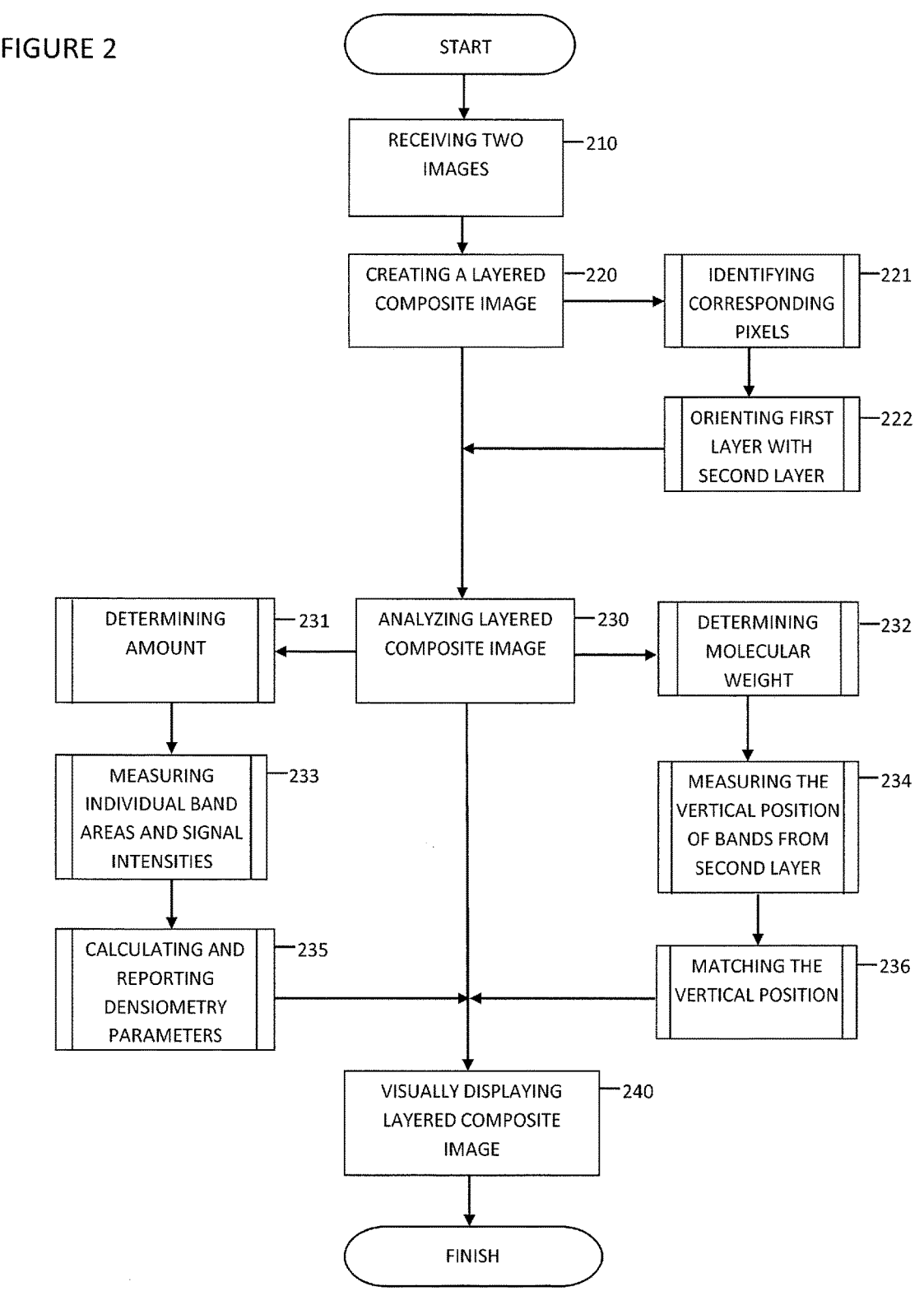
FIG. 2 is an exemplary flowchart showing one embodiment of the method and system.
Figure 3:
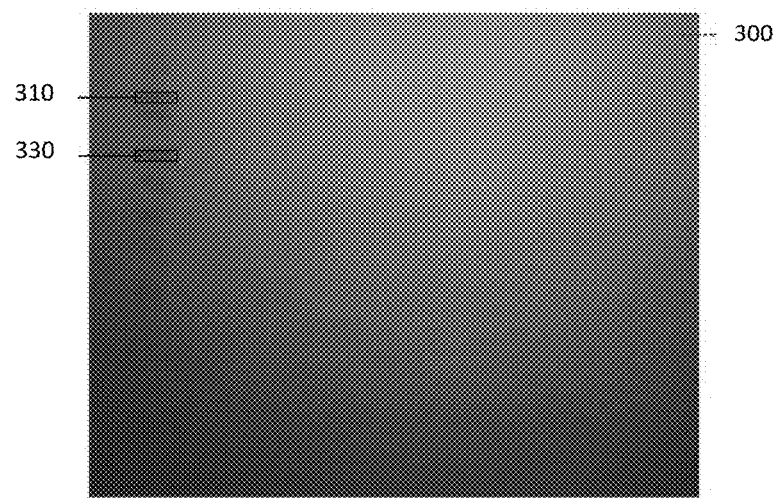
FIG. 3 is digital image of a Western blot with bands captured by white light illumination.
Figure 4:
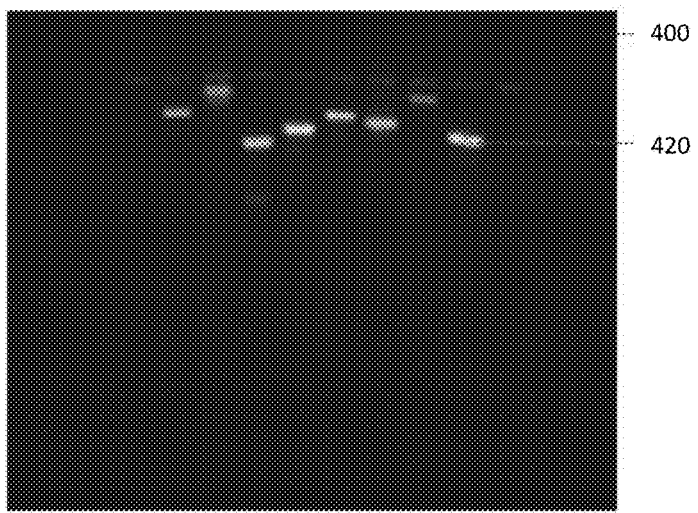
FIG. 4 is a digital image of a Western blot with bands captured by chemiluminescence.
Figure 5:
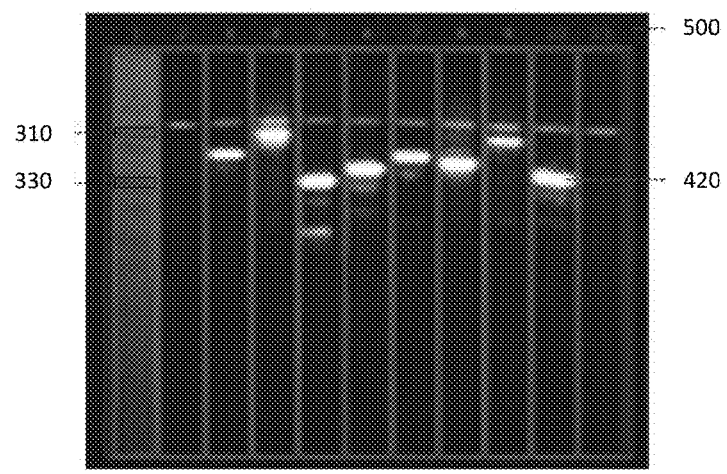
FIG. 5 is a digital image of a layered composite image where the leftmost lane is taken from FIG. 3, and the other lanes are taken from FIG. 4.
Figure 6:
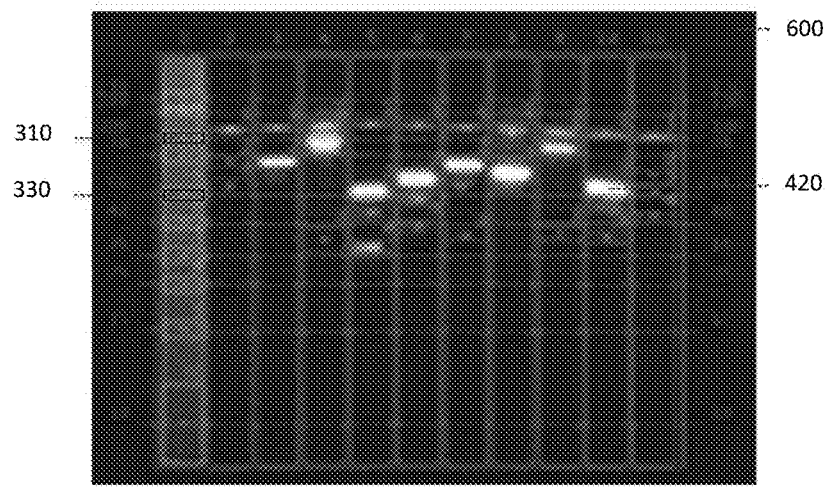
FIG. 6 is a digital image similar to FIG. 5 with horizontal lines on each band from FIG. 3.
Figure 7:
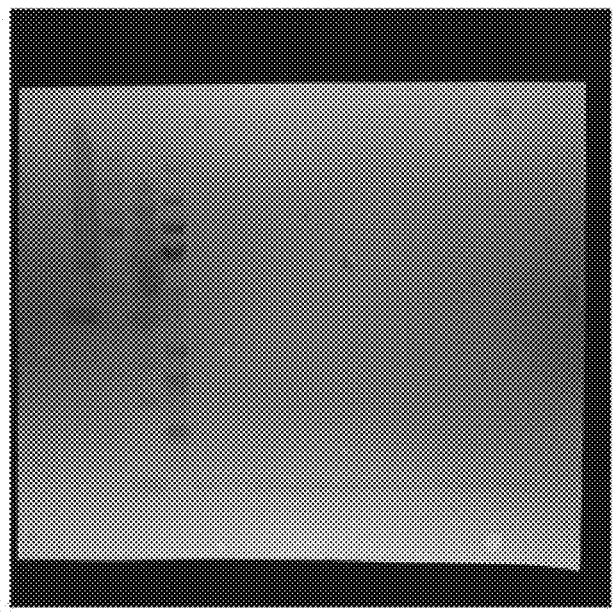
FIG. 7 is digital image of a Western blot with bands captured by white light illumination.
Figure 8:
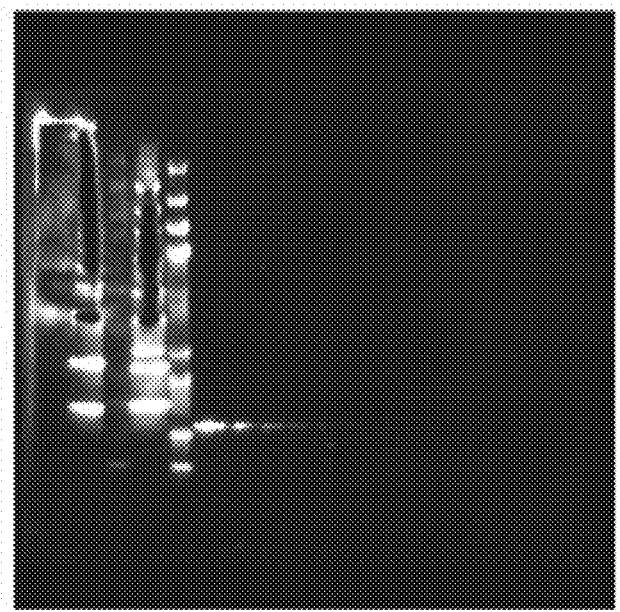
FIG. 8 is digital image of a Western blot assay with bands captured by chemiluminescence.
Figure 9:
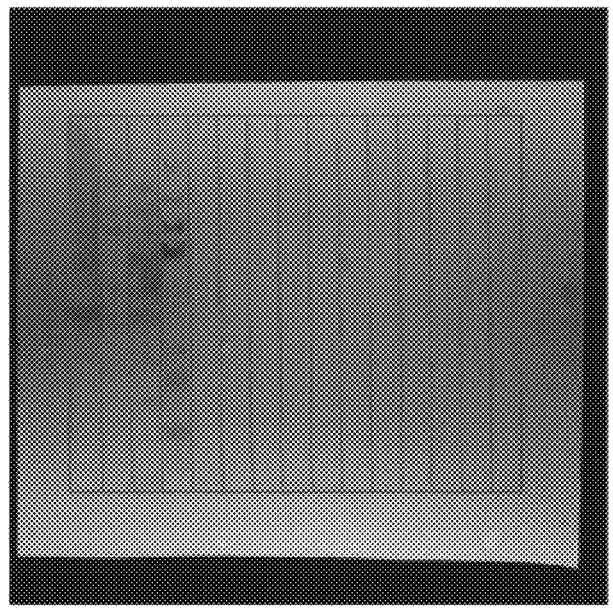
FIG. 9 is digital image similar to FIG. 7 with lanes defined over the image.
Figure 10:
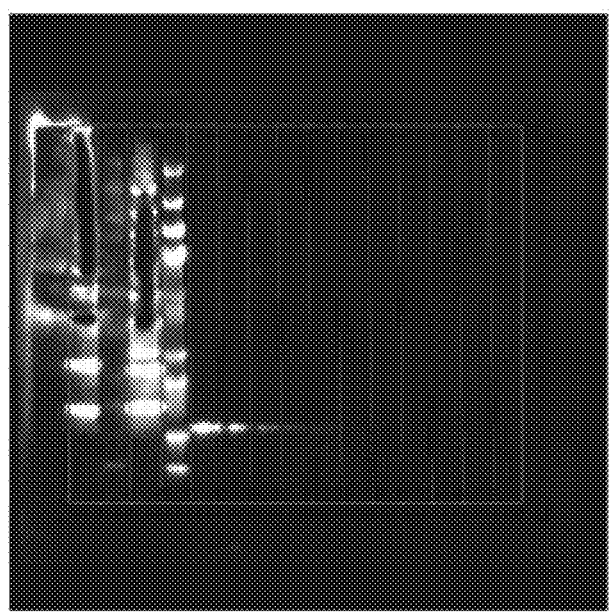
FIG. 10 is digital image similar to FIG. 8 with lanes defined over the image.
Figure 11:
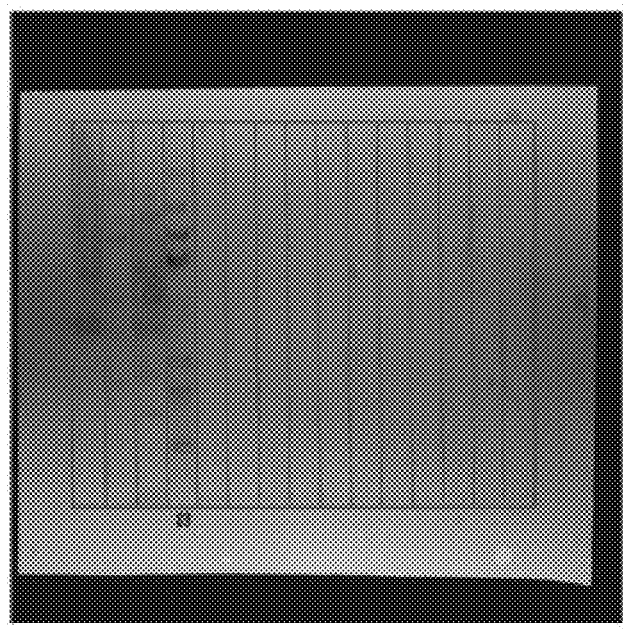
FIG. 11 is a digital image similar to FIG. 9 with a user-identified lane to use as the visible molecular weight standard.
Figure 12:
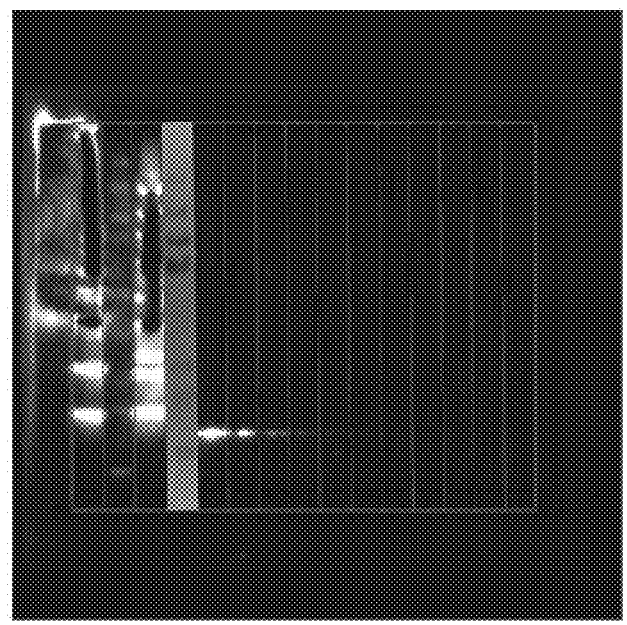
FIG. 12 is a digital image similar to FIG. 10 where the lane marked in FIG. 11 as the visible molecular weight standard is overplayed in the correct lane of the chemiluminescently visualized image of the sample substrate.

As a person of ordinary skill in the art appreciates, specific functional blocks presented in relation to the inventive methods and systems are programmable as separate modules or functional blocks of code. These modules are capable of being stored in a one- or multiple-computer storage media in a distributed manner. In one embodiment, these modules are executed to perform the inventive method and system in whole or in part on a single computer. In one embodiment, these modules are executed to perform the inventive methods and systems on multiple computers that cooperatively execute the modules. In one embodiment, the programs are executed in a virtual environment, where physical hardware operates an abstract layer upon which the inventive methods and systems are executed in whole or in part across one or more physical hardware platforms. In one embodiment, with reference to FIGS. 2, 3, and 4, the inventive methods and systems provides enhanced analysis, through a series of steps, of bands that have been electrophoretically separated in a substrate. In the first step, two images of the substrate are received 210. The first image 300 is composed of bands 310, 330 captured by a first visualizing means such as white light illumination, and the vertical position of each of the electrophoretic bands 310, 330 is associated with a predefined molecular weight. The second image 400 is composed of bands 420 captured by a second visualizing means such as lack of illumination, e.g., no illumination for chemiluminescence, ultraviolet illumination, LED white illumination or other white epi-illumination modules, or LED color illumination; with ultraviolet, color, or white illumination optionally in conjunction with an emission filter. Next, a layered composite image is created 220 from the first image 300 and second image 400. Finally, the layered composite image is analyzed 230 to determine information about the samples in the substrate.

In one embodiment, the creating step 220 includes identifying 221 corresponding pixels from a subset of pixels from the first layer that correspond to a subset of pixels from the second layer; and then orienting 222 the first layer with the second layer based at least on an alignment of the corresponding pixels, resulting in the creation of the layered composite image.

In one embodiment, the orienting step 222 includes mapping the positions of a first set of pixels to the positions of a second set of pixels, where the first set of pixels substantially define the first layer and the second set of pixels substantially define the second layer. Mapping is performed in accord with the positions of the corresponding pixels resulting in a common coordinate system between the first layer and the second layer.

In one embodiment, noise is reduced on a single layer relative to itself, or is reduced on both layers but each layer is relative to itself.

In one embodiment, the layered composite image is visually displayed 240 to a user.

In one embodiment, the analyzing step 230 compares information between the first image 300 and the second image 400 and includes determining molecular weight 232 by measuring 234 the vertical position of a second band 420 from the second layer; then matching 236 the vertical position of the second band 420 to a substantially equivalent vertical position of a first band 330 on the vertical weight scale from the first layer, and identifying a molecular weight 232 associated with the second band 420.

In one embodiment, the analyzing step 230 includes identifying a molecule, e.g., a protein, associated with the molecular weight, and associating the second band with the identified molecule.

In one embodiment, the analyzing step includes repeating the previous analyzing steps 230 for those second bands 420 not associated with a molecule. The repeating step can continue until sufficient second bands 420 have been associated with molecules that their source is established with reasonable certainty, as known by one skilled in the art.

In one embodiment, the analyzing step 230 calculates information within the first image 300, including measuring an individual area and signal intensity 233, and purity of each of the first bands 310, 330, and reporting such densitometry analysis parameters 235 in a table. Multiple densitometry parameters are reported, including volume (signal intensity), area, density (intensity/area), median signal intensity value, background corrected intensity and density values (calculated by default and optionally user-defined background methods), and percent purity calculated by band (single band signal intensity divided by the total intensity of all bands within the lane), and by lane (single band signal intensity divided by the total intensity within the lane). Optionally, relative and absolute amounts 231 can also be analyzed. The relative amount of each band is calculated by comparing its signal intensity to that of other bands. The absolute amount of each band is calculated by comparing signal intensity to bands of known quantity.

In one embodiment, the analyzing step 230 calculates information within the second image 400, including measuring an individual area and signal intensity 233, and purity for each of the second bands 420, and reporting such densitometry analysis parameters 235 in a table. Multiple densitometry parameters are reported, including volume (signal intensity), area, density (intensity/area), median signal intensity value, background corrected intensity and density values (calculated by default and optionally user-defined background methods), and percent purity calculated by band (single band signal intensity divided by the total intensity of all bands within the lane), and by lane (single band signal intensity divided by the total intensity within the lane). Optionally, relative and absolute amounts 231 can also be analyzed. The relative amount of each band is calculated by comparing its signal intensity to that of other bands. The absolute amount of each band is calculated by comparing signal intensity to bands of known quantity.

In one embodiment, an imaging device is controlled to capture the first image 300 by the first visualizing means, then to capture the second image 400 by a second visualizing means.

In use, a user opens the two images (for simplicity, the image with no illumination e.g., chemiluminescent is noted as Image #1, and the image with white light illumination is noted as Image #2) for overlay and adjusts the contrast on Image #1. The user then creates and places a lane frame on Image #1 and adjusts the lanes to fit the imaged sample, e.g., modify lane frame height, width, and placement; apply lane skew if necessary, etc. The user then indicates to the software the identity of Image #2, the location of the lane to be replaced on Image #1, optionally the identity of the molecular weight marker which can be obtained from a dropdown menu of preloaded markers or imported, the regression method to be applied for molecular weight determination, and performs automatic band identification which uses an optimized algorithm for object detection and identification. The overlaid lane is depicted on the image once the user establishes the location of the lane to be overlaid and the identity of Image #2.

Figure 13:
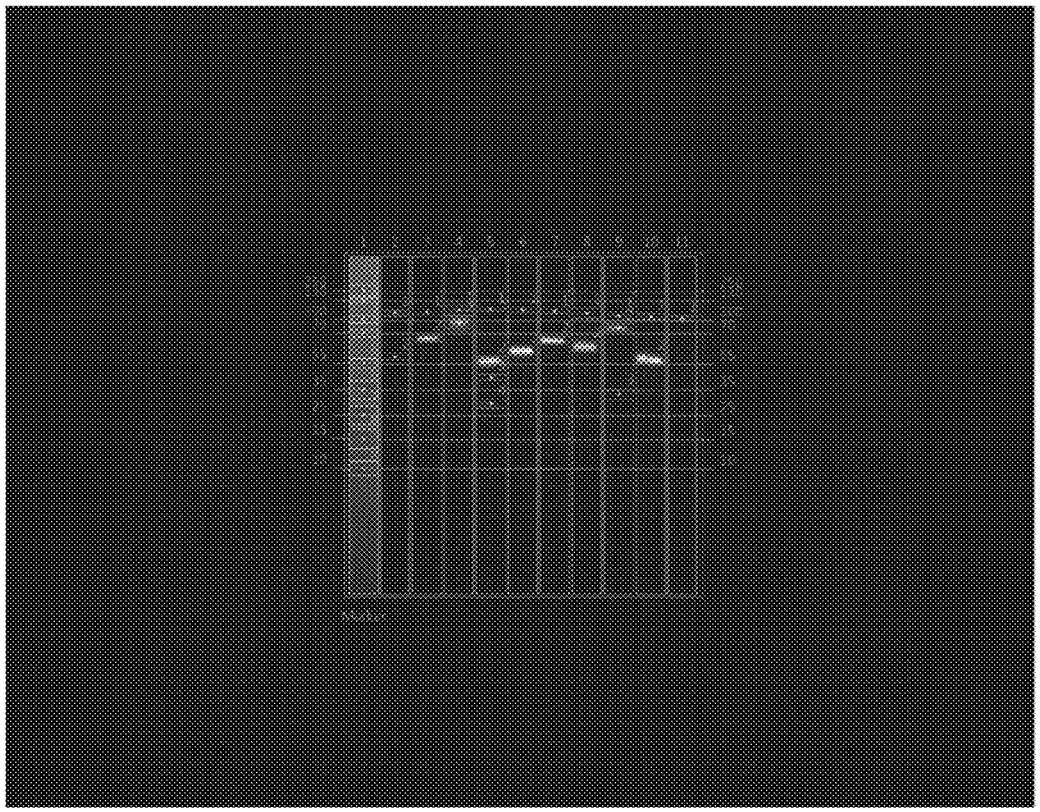
FIG. 13 is a sample analysis report.
Figure 14A:
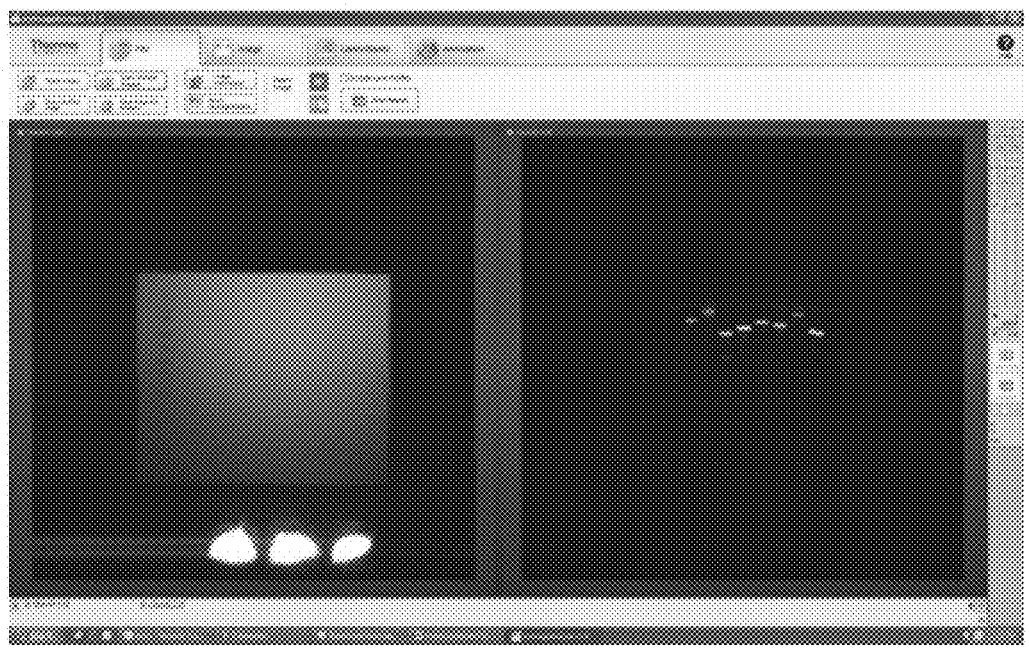
FIGS. 14A-I show steps in a sample procedure.

One embodiment uses the inventive methods and systems with the MYECL™ Imager (Thermo Fisher Scientific) implemented in the automatic lane and band identification in the myImageAnalysis™ Software (Pierce Biotechnologies, Inc., Rockford Ill.). Software for the method is both separately available and as a component of the MYECL™ Imager, and is capable of preparing an analysis report, a sample of which is shown in FIG. 13, with the overlaid image and analysis table, or the overlaid image alone, and exporting this report to MicroSoft Word, MicroSoft PowerPoint, Adobe, etc. The procedure may include the following steps, with illustrations as shown in FIGS. 14A-I Open chemiluminescent and visible images (ChemiS and ChemiV image files from myECL® Imager) (FIG. 14A).

Figure 14B:
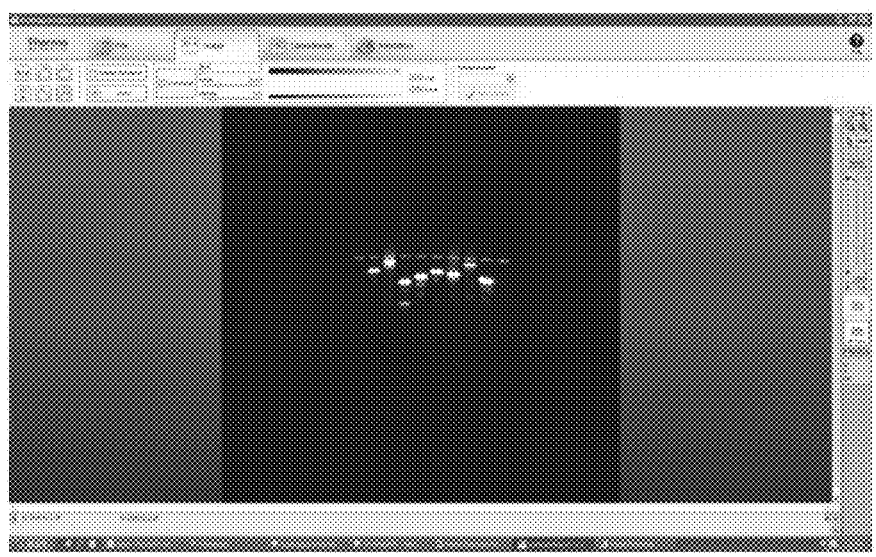

Select the Image tab and adjust chemiluminescent image contrast with the White Level slider bar or Auto Adjust button until bands are visible (FIG. 14B).

Figure 14C:
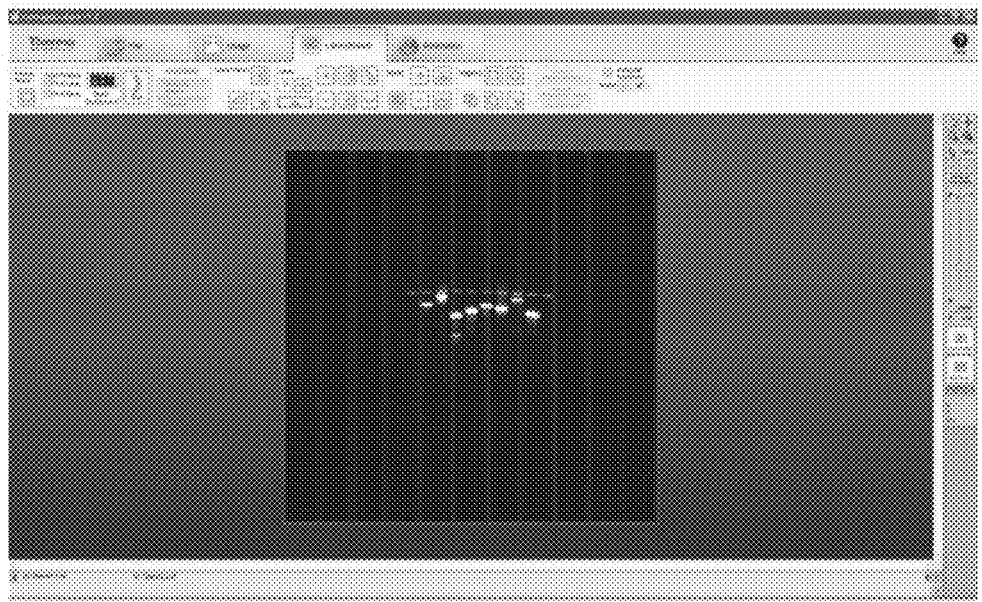

In the Lanes/Bands subtab, manually add the appropriate number of lanes to the chemiluminescent image, including the lane which contains the colorimetric molecular weight marker (FIG. 14C).

Figure 14D:
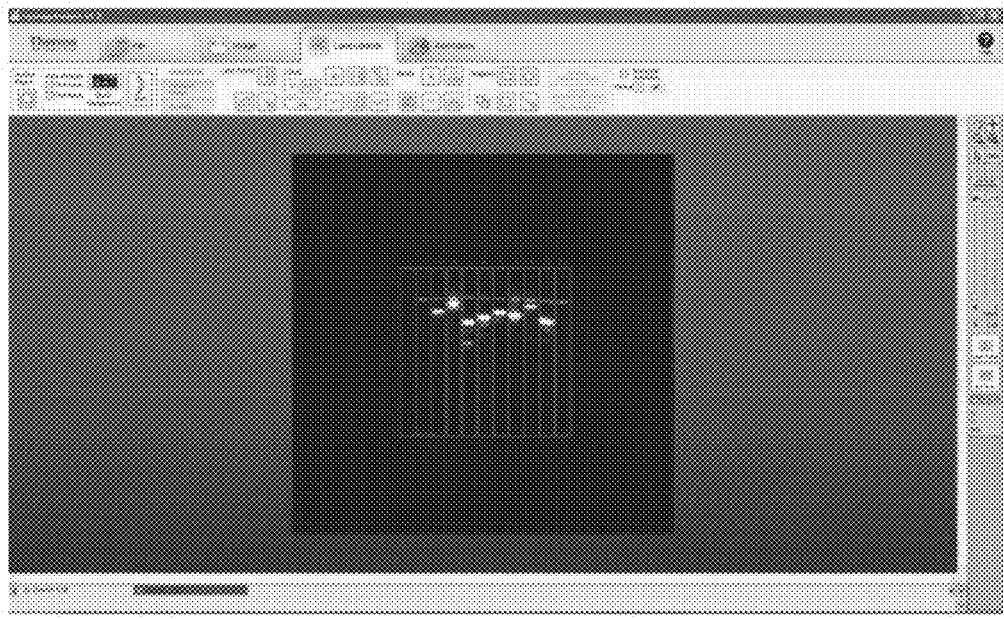

Resize the Lane Frame to fit the imaged blot; adjust lane placement, width and/or skew as necessary (FIG. 14D).

Figure 14E:
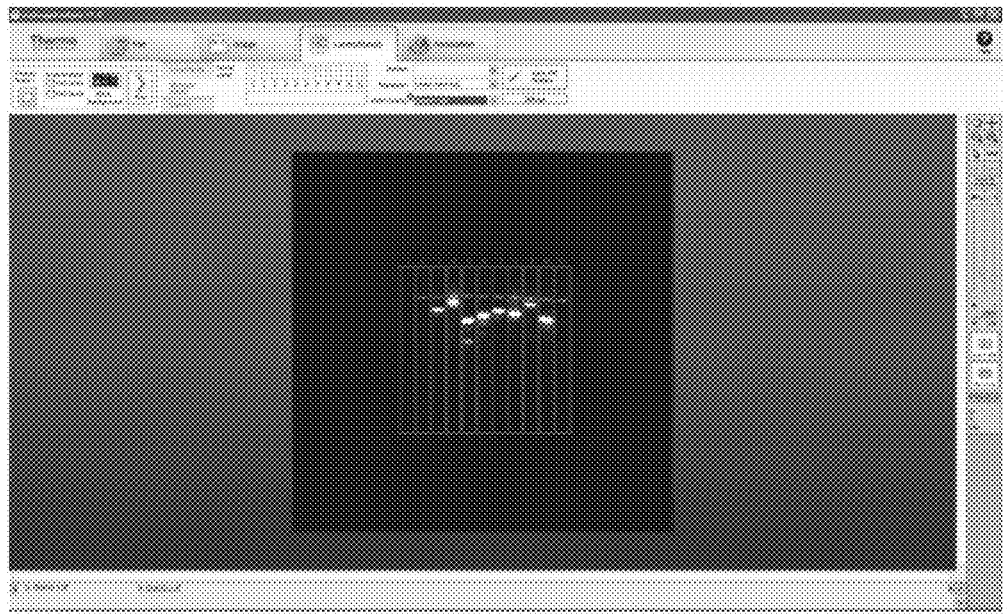

In the Molecular Weight subtab, select the visible image file name in the MWM Overlay drop-down menu (FIG. 14E).

Figure 14F:
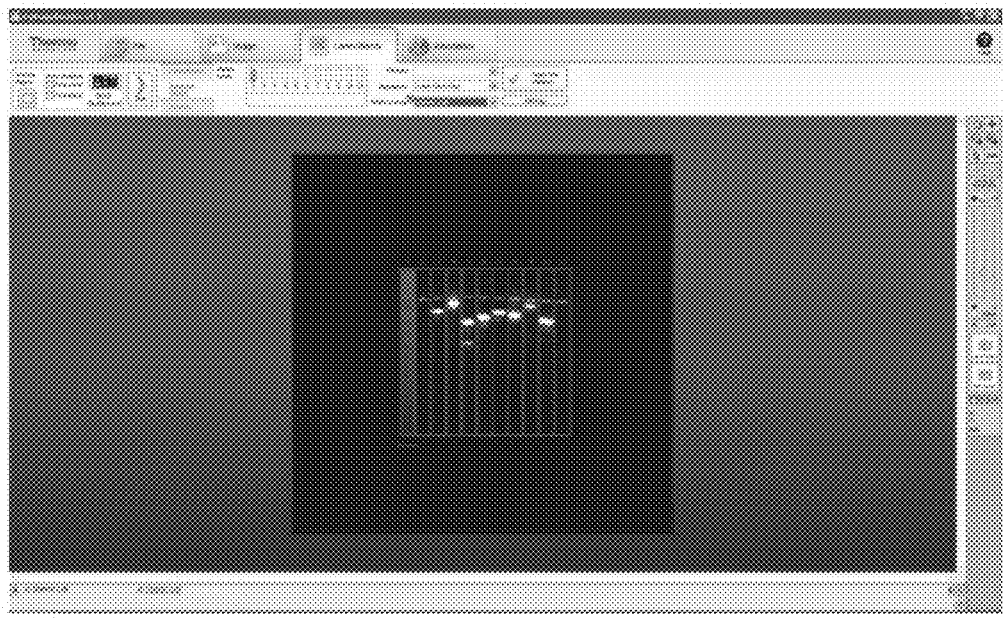

In the Marker Lanes box, select the lane containing the molecular weight marker (FIG. 14F).

In the Markers drop-down menu, select the appropriate molecular weight marker. In the Regression drop-down menu, select the appropriate regression method.

Figure 14G:
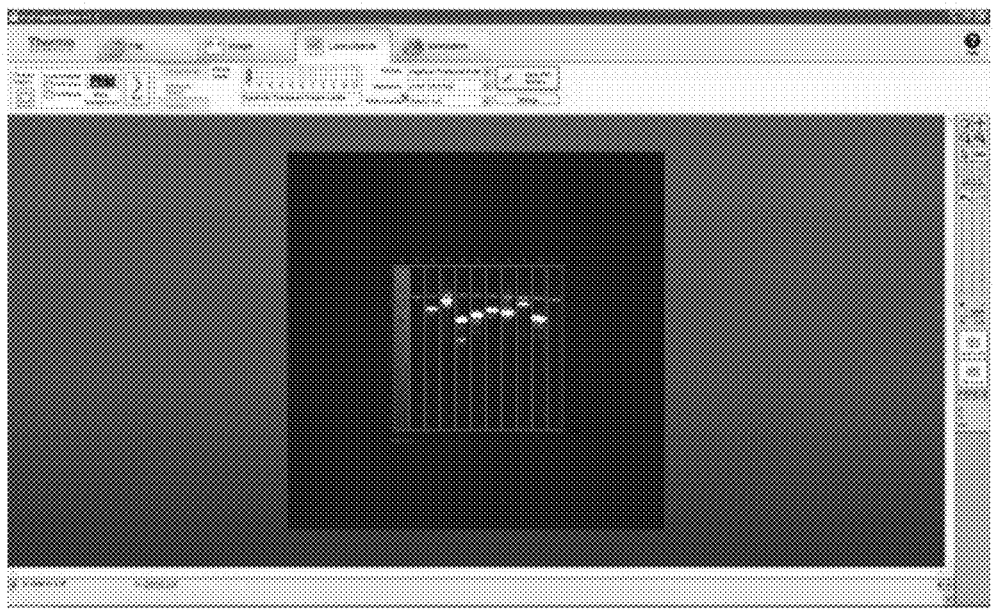

Select Apply MW Markers (FIG. 14G).

Figure 14H:
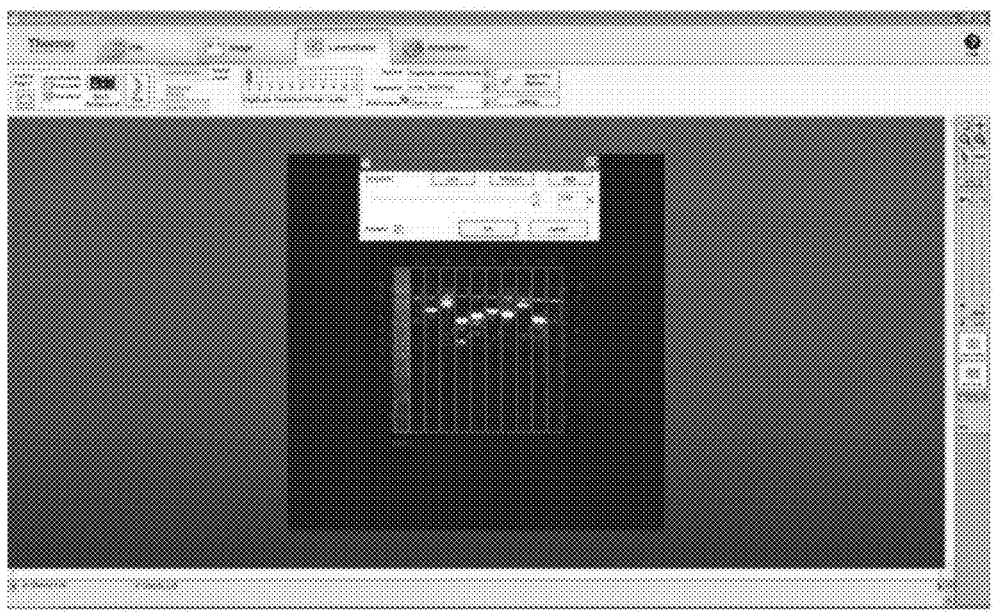

Check the Find Bands box in the Auto-Analyze module and select Run (FIG. 14H).

Adjust the sensitivity level in the Sensitivity tool to identify all marker bands and bands of interest. Select OK. Note: The sensitivity level may need to be 100% for all marker bands to be identified. Remove undesired bands in the chemiluminescent image with the Delete Bands button in the Lanes/Bands subtab.

Figure 14I:
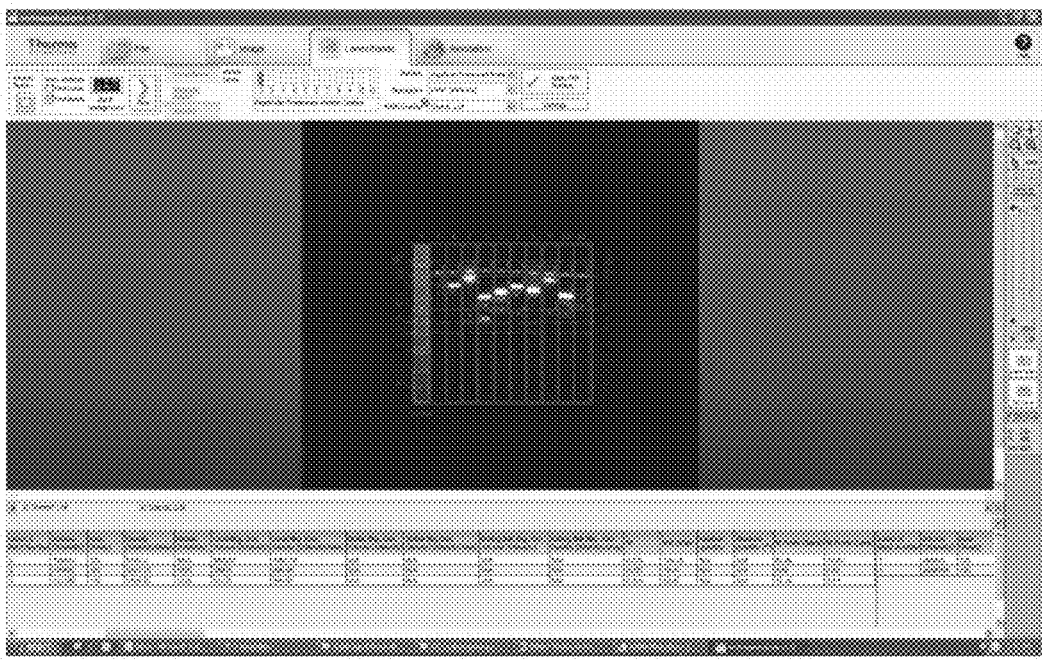

The result is a display of the colorimetric molecular weight marker image within the chemiluminescent image. Molecular weight determination is performed for the located bands and results are displayed in the Analysis Table. Accurate densitometry analysis can only be performed on the chemiluminescent image. Pixel intensities in the marker lane on the Analysis Table are from the visible image; all other pixel intensities in the Analysis Table are from the chemiluminescent image (FIG. 14I).

Imager automatically acquiring a visible image of a blot when the instrument is in chemiluminescent acquisition mode.

The embodiments described in the specification are only specific embodiments of the inventors who are skilled in the art and are not limiting. Therefore, various changes, modifications, or alterations to those embodiments may be made without departing from the spirit of the invention or the scope of the following claims.

What is claimed is:

1. A method for improving analysis of electrophoretic bands in a substrate, the method comprising
receiving a first image of the substrate and a second image of the substrate, the first image comprising a plurality of first electrophoretic bands captured by a first visualizing means, and the second image comprising a plurality of second electrophoretic bands captured by a second visualizing means, where the vertical position of each of the plurality of first electrophoretic bands is associated with a predefined molecular weight such that the first image represents a vertical weight scale;
creating a layered composite image where the first image defines a first layer of the layered composite image and the second image defines a second layer of said layered composite image; and
analyzing the layered composite image by a molecular weight analysis and a densitometry analysis, where the molecular weight analysis includes performing a molecular weight determination by comparing information between the first image and the second image as it exists in the layered composite image, and where the densitometry analysis includes performing a densitometry determination by comparing information only within the second layer.

2. The method of claim 1 where the creating step further comprises
identifying a plurality of corresponding pixels defined from a subset of pixels from the first layer that correspond to a subset of pixels from the second layer; and
orienting the first layer with the second layer based at least on an alignment of the plurality of corresponding pixels, resulting in creating the layered composite image.

3. The method of claim 2 where the orienting step further comprises
mapping the positions of a first set of pixels to the positions of a second set of pixels, where the first set of pixels substantially defines the first layer, and the second set of pixels substantially defines said second layer, where mapping is performed in accordance with the positions of the plurality of corresponding pixels resulting in a common coordinate system between the first layer and the second layer.

4. The method of claim 1 where the molecular weight determination comprises
determining the vertical position of a second electrophoretic band from the second layer;
matching the vertical position of the second electrophoretic band to a substantially equivalent vertical position on the vertical weight scale from the first layer; and
identifying a molecular weight associated with the second electrophoretic band.

5. The method of claim 4 where the analyzing step further comprises
identifying a molecule associated with the molecular weight; and
associating the second electrophoretic band with the identified molecule.

6. The method of claim 5 where the analyzing step further comprises repeating the previous analyzing steps for those second electrophoretic bands not associated with a molecule.

7. The method of claim 6 wherein the repeating step continues until a sufficient number of second electrophoretic bands have been associated with molecules to establish a source of the second electrophoretic bands.

8. The method of claim 1 where the analyzing step compares information within the first image and comprises
measuring an individual area for each of the plurality of first electrophoretic bands;
measuring signal intensity for each of the plurality of first bands; and
calculating a percent purity for each band.

9. The method of claim 1 where the densitometry determination comprises
measuring an individual area for each of the plurality of second electrophoretic bands;
measuring signal intensity for each of the plurality of second bands; and
calculating a percent purity for each band.

10. The method of claim 1 further comprising controlling an imaging device to capture the said first image by a first visualizing means, then to capture the second image by a second visualizing means.

11. A non-volatile computer readable storage medium having data stored therein representing software executable by a computer, the software including instructions to provide improved analysis of electrophoretic bands in a substrate, the storage medium comprising
   instructions for receiving a first image of the substrate and a second image of the substrate, where the first image comprises a plurality of first electrophoretic bands captured by a first visualizing means, and the second image comprises a plurality of second electrophoretic bands captured by a second visualizing means,
where the vertical position of each of the plurality of first electrophoretic bands is associated with a predefined molecular weight such that said first image represents a vertical weight scale;
   instructions for creating a layered composite image, where the first image defines a first layer of the layered composite image and the second image defines a second layer of the layered composite image; and
   instructions for analyzing the layered composite image, where the instructions for analyzing comprise a first set of instructions and a second set of instructions,
   where the first set of instructions include performing a molecular weight determination by comparing information between the first image and the second image as it exists in the layered composite image, and
   where the second set of instructions include performing a densitometry determination by comparing information only within the second layer.

12. The non-volatile computer readable storage medium of claim 11 where the instructions for creating a layered composite image further comprise
   instructions for identifying a plurality of corresponding pixels defined from a subset of pixels from the first layer that correspond to a subset of pixels from the second layer; and
   instructions for orienting the first layer with the second layer based at least on an alignment of the plurality of corresponding pixels, resulting in the creation of the layered composite image.

13. The non-volatile computer readable storage medium of claim 12 where the instructions for orienting the first layer with the second layer further comprise
   instructions for mapping the positions of a first set of pixels to the positions of a second set of pixels, where the first set of pixels substantially define the first layer, and the second set of pixels substantially define the second layer, where the mapping is performed in accord with the positions of the plurality of corresponding pixels, resulting in a common coordinate system between the first layer and the second layer.

14. The non-volatile computer readable storage medium of claim 11 where the first set of instructions for analyzing comprise
   instructions for determining the vertical position of a second electrophoretic band from the second layer;
   instructions for matching the vertical position of the second electrophoretic band to a substantially equivalent vertical position on the vertical weight scale from the first layer; and
   instructions for identifying a molecular weight associated with the second electrophoretic band.

15. The non-volatile computer readable storage medium of claim 11 where the instructions for analyzing are directed to comparing information within the first image and comprises
   instructions for measuring an individual area for each of the plurality of first electrophoretic bands;
   instructions for adding each of the individual areas to acquire a total area; and
instructions for calculating a percent of total weight for each of the plurality of first electrophoretic bands, where each calculation takes the individual area for each band and divides that value by the total area for all bands.

16. The non-volatile computer readable storage medium of claim 11 where the second set of instructions for analyzing comprise
   instructions for measuring an individual area for each of the plurality of second electrophoretic bands;
   instructions for adding each of the individual areas to acquire a total area; and
   instructions for calculating a percent of total weight for each of the plurality of second electrophoretic bands, where each calculation takes the individual area for each band and divides that value by the total area for all bands.

17. The non-volatile computer readable storage medium of claim 11 further comprising instructions for controlling an imaging device to capture the first image by the first visualizing means, and instructions to capture the second image by a second visualizing means.

18. A system for improving analysis of electrophoretic bands in a substrate, the system comprising
   an imaging device adapted to capture a plurality of digital images including a first image of the substrate and a second image of the substrate,
      where the imaging device captures the first image by a first visualizing means and immediately thereafter automatically captures the second image by a second visualizing means, where the first image comprises a plurality of first electrophoretic bands and said second image comprises a plurality of second electrophoretic bands,
      where the vertical position of each of the plurality of first electrophoretic bands is associated with a predefined molecular weight such that the first image represents a vertical weight scale;
   a computer adapted for communicating with the imaging device, the computer having at least one processor to execute logic instructions associated with at least one computer software program and a memory for storing the logic instructions,
      where the memory stores the first image and the second image received from the imaging device,
      where at least one computer software program contains instructions to create a layered composite image from the first image and the second image,
      where the first image defines a first layer of the layered composite image and the second image defines a second layer of the layered composite image; and
      where the at least one computer software program contains instructions to analyze the layered composite image, where the instructions for analyzing comprise a first set of instructions and a second set of instructions, where the first set of instructions include performing a molecular weight determination by comparing information between the first image and the second image as it exists in the layered composite image, and where the second set of instructions include performing a densitometry determination by comparing information only within the second layer; and a user interface adapted to communicate at least one determination.

19. The system of claim 18 where the computer further comprises at least one computer software program for noise reduction, adapted to reduce noise on a single layer.

20. The system of claim 18 where the user interface comprises a visual display for displaying the layered composite image to a user.

* * * * *